(12) United States Patent
Lefoulon et al.

(10) Patent No.: US 7,999,009 B2
(45) Date of Patent: Aug. 16, 2011

(54) STRONTIUM SALTS OF SULPHONIC ACIDS, A PROCESS FOR THEIR PREPARATION AND PHARMACEUTICAL COMPOSITIONS CONTAINING THEM

(75) Inventors: Francois Lefoulon, Orleans (FR); Yves Rolland, Vanves (FR)

(73) Assignee: Les Laboratoires Servier, Suresnes Cedex (FR)

( * ) Notice: Subject to any disclaimer, the term of this patent is extended or adjusted under 35 U.S.C. 154(b) by 1016 days.

(21) Appl. No.: 11/784,642

(22) Filed: Apr. 9, 2007

(65) Prior Publication Data

US 2007/0244191 A1    Oct. 18, 2007

(30) Foreign Application Priority Data

Apr. 12, 2006  (FR) ..................................... 06 03224

(51) Int. Cl.
*C07C 309/04* (2006.01)
*C07C 309/05* (2006.01)
*C07C 309/13* (2006.01)
*A61K 31/131* (2006.01)
*A61K 31/10* (2006.01)
*A61P 19/10* (2006.01)

(52) U.S. Cl. ......... 514/711; 514/665; 562/101; 562/104

(58) Field of Classification Search ................. 562/101, 562/104; 514/665, 711

See application file for complete search history.

(56) References Cited

U.S. PATENT DOCUMENTS

| 3,236,708 | A | * | 2/1966 | Tillis | ............................. | 216/105 |
| 4,199,513 | A | * | 4/1980 | De Jong et al. | ............... | 549/208 |
| 7,335,686 | B2 | * | 2/2008 | Rao et al. | ...................... | 514/562 |

FOREIGN PATENT DOCUMENTS

| EP | 0415850 | 3/1991 |
| WO | 2004/098618 | 11/2004 |

OTHER PUBLICATIONS

Ambronn (Zeitschrift fuer Kristallographie und Mineralogie, 1913, 52, pp. 48-57). See STN printout pp. 1-17.*
Portillo (Anales de la Real Sociedad Espanola de Fisica y Quimica, 1929, 27, pp. 351-357).*
Lehmann et. al.. (Zietschrift fuer Anorganische und Allgemeine Chemie, 1967, 355(5-6), pp. 225-229).*
Mantovani et. al. (Zeitschrift fuer die Zuckerindustrie, 1977, 27(5), pp. 286-290).*

Dean, W. (<http://www.worldhealth.net/news/strontium_breakthrough_against_osteoporo/>, downloaded May 4, 2010).*
Fe. McCaslin, et al., "The effect of strontium lactate in the treatment of osteoporosis" Proceedings of the Staff Meetings of the Mayo Clinic, vol. 34, No. 13, p. 329-334, 1959.
B. Von Bitto, "Ein beitrag zur kantniss der alfa-Sulfonormacapronsaure und ihrer salze", Berichte Der Deutschen Chemischen Gesellschaft, vol. 63, p. 1642-1648, 1897.
Jiwen Cai, et al., Solid-state structures of group 1 and group 2 metal 1,5-naphthalenedisulphonates: systematic investigation of lamellar three-dimensional networks constructed by metal arenedisuiphonate: Acta Crystallographica, Section B, Structural Science, vol. 57, No. 4, p. 520-530, 2001.
H.D. Fierz-David, et al., :Uber die disulfration des naphthalines Helvetica Chimic Acta, vol. 6, No. 1, p. 1133-1146, 1923.
F. Ephraim, et al., : Uber die salze einiger aromatischer sulfonsauren und deren Loslichkeit: Helvetica Chimica Acta, vol. 8 No. 1, p. 229-241, 1925.
Database Caplus Chemical Abstracts Service, Columbus, Ohio, XP002411199, Database accession No. 1981:24268, 1980.
W. Hemminger, "Thermal Analysis" Proceedings of the 6*th* International Conference on Thermal Analysis, vol. 2, p. 425-430, 1980, abstract.
Database Caplus Chemical Abstracts Service, Columbus, Ohio, XP002411200, Database accession No. 1963:81066, 1962.
Xu-Jie Yang, et al., "Preparation and characterization of metal containing aromatic polyimides" Journal of Applied Polymer Science, vol. 77, No. 11, p. 2363-2369, Sep. 2000.
V. Cupr, et al., "Aminobenzolsulfonate der zweiwertigen elementen" Journal Fuer Praktische Chemie, vol. 142, No. 1, p. 6-10, Jan. 1935.
V. Curp, et al., "Aromatischen sulfonate der elementen der zweiten gruppe des periodischen systems", Journal Fuer Praktische Chemie, vol. 139, No. 7-9, p. 245-253, Feb. 1934.
Database beilstein, Beilstein Institut Zur Forderung Der Chemischem Wisssenschaften, Frankfurt-Am-Main, Germany, Datbase accession No. Beilstein Registry No. 3809627, 1991.
Yufeng Liu, et al., : First hydrocalcite-like sulphonate coordination network incorporation robust cationic layers and flexible interlayer interactions: Inorganic Chemistry, vol. 44, No. 11, p. 3890-3895, May 2005.
French Preliminary Search Report for FR0603224 of Dec. 13, 2006.

* cited by examiner

Primary Examiner — Susanna Moore
(74) Attorney, Agent, or Firm — Hueschen and Sage

(57) ABSTRACT

Strontium salts of the sulphonic acids of formula (I):

$$A\text{-}B\text{---}SO_3H \qquad (I),$$

wherein:
A represents a group selected from OH, $NH_2$, $SO_3H$ and $CO_2H$,
B represents an arylene group or an optionally substituted linear or branched $C_1$-$C_{12}$alkylene chain wherein one or more carbon atoms of the alkylene chain may be optionally replaced by an oxygen atom, by a nitrogen atom or by an $SO_2$ group.

Medicinal products containing the same which are useful in the treatment of osteoarthritis and osteoporosis.

5 Claims, No Drawings

STRONTIUM SALTS OF SULPHONIC ACIDS, A PROCESS FOR THEIR PREPARATION AND PHARMACEUTICAL COMPOSITIONS CONTAINING THEM

The present invention relates to new strontium salts of sulphonic acids, to a process for their preparation and to pharmaceutical compositions containing them. A large number of mineral and organic salts of strontium are already known from the literature. Amongst the compounds of sulphonic acid, strontium bis(aminomethane-sulphonate), and the use thereof in photographic papers, have already been described in U.S. Pat. No. 4,419,433. Strontium methanedisulphonate has been described in the publication Recueil: *Journal of the Royal Netherlands Chemical Society* 1981, 100(12), 449-452. Strontium m-benzenedisulphonate has been described in the publication *J. Phys. Chem.* 1963, 67, 337-339. Strontium 6-sulphonatohexanoate has been described in the publication *Berichte* 1897, 63, 1642-48. Strontium 1,5-naphtalenedisulphonate has been described in the publicaion *Acta Cryst.* 2001, 57(4), 520-530. Strontium 1,6-naphthalenedisulphonate has been described in the publication *Helv. Chim. Acta* 1923, 6(1), 1133-1146. Strontium bis(6-hydroxy-2-naphthalenesulphonate) has been described in the publication *Helv. Chim. Acta* 1925, 8(1), 229-241. Strontium 2-oxo-1,3-propanedisulphonate has been described in Therm. Anal. 1980, 6th, Vol 2, 425-430. Strontium hydroxymethanesulphonate has been described in the patent specification JP 37006516. Strontium bis(4-aminobenzene-sulphonate) has been described in the publications *J. Applied Polymer Sc.* 2000, 77(11), 2363-69 and *J. Prakt. Chem.* 1934, 245-253. Strontium bis(2-aminobenzene-sulphonate) and strontium bis(3-aminobenzenesulphonate) have been described in the publication *J. Prakt. Chem.* 1935, 6-10. Strontium 1,2-ethanedisulphonate has been described in the publication *Kristallogr. Kristallgeom. Kristallchem.* 1913, 51, 502. Strontium 3-amino-3-carboxy-1-propanesulphonate chloride has been described in the publication *Inorg. Chem.* 2005, 44(11), 3890-95.

The use of strontium salts for therapeutic purposes has already formed the subject of publications and patents. For example, U.S. Pat. No. 4,152,431 describes alkali metal salts that can be used in the treatment of inflammation. Patent application WO-94/09798 presents sulphate complexes of various metals which are active in the treatment of skin disorders. The works of Olle Svensson et al (*Acta Path. Microbiol. Immunol. Scand.*, Sect. A, 1985, 93, 115-120) demonstrate that strontium plays a part in some rickets cases.

Strontium ranelate and its use in the treatment of osteoporosis have been described in patent specification EP 0 415 850.

The present invention relates to new strontium salts derived from sulphonic acid, and to the use thereof in the treatment of osteoarthritis and osteoporosis.

Osteoporosis is a decrease in calcium mineralisation in the skeleton.

Like all living tissue, bone is subject to a continual destruction-reconstruction process bone remodelling. It is characterised first of all by a phase of resorption of the old bone matrix by osteoclasts, followed by a phase of reparation by the formation of the protein matrix by osteoblasts, which will then be mineralised. In a young person, the bone equilibrium is balanced but, with age, an imbalance occurs between bone resorption and bone formation to the detriment of the latter.

Osteoarthritis is a degenerative pathology that affects articular cartilage in more than 50% of the population above the age of 65. It is characterised always by a degradation of the cartilaginous matrix surrounding the chondrocytes. In non-pathological conditions, those cells ensure the homeostasis of cartilage. On the other hand, under the effect of a certain number of factors (biomechanical and/or biochemical), chondrocytes are at the origin of the degradation of that surrounding tissue, because in such cases they secrete metalloproteases, which degrade type II collagen and proteoglycans, the matrix components characteristic of cartilage.

More especially, the present invention relates to strontium salts of the sulphonic acids of formula (I):

wherein:
A represents a group selected from OH, $NH_2$, $SO_3H$ and $CO_2H$,
B represents an arylene group or a linear or branched $C_1$-$C_{12}$alkylene chain optionally substituted by one or more groups selected from hydroxy, oxo, amino, $SO_3H$ and $CO_2H$ and in which one or more carbon atoms is optionally replaced by an oxygen atom, by a nitrogen atom or by an $SO_2$ group, with the exclusion of strontium bis(aminomethanesulphonate), strontium methane-disulphonate, strontium 1,3-benzenedisulphonate, strontium 6-sulphonatohexanoate, strontium 1,5-naphthalenedisulphonate, strontium 1,6-naphthalenedisulphonate, strontium bis(6-hydroxy-2-naphthalenesulphonate), strontium 2-oxo-1,3-propane-disulphonate, strontium hydroxymethanesulphonate, strontium bis(4-aminobenzene-sulphonate), strontium bis(2-aminobenzenesulphonate), strontium bis(3-aminobenzene-sulphonate), strontium 1,2-ethanedisulphonate and strontium 3-amino-3-carboxy-1-propanesulphonate chloride.

Arylene is understood to be phenylene, biphenylylene or naphthylene, each of those groups being optionally substituted by one or more identical or different groups selected from linear or branched $C_1$-$C_6$alkyl, OH, $NH_2$, $SO_3H$ and $CO_2H$.

One embodiment of the present invention concerns strontium salts of the compounds of formula (I) wherein A represents $NH_2$ or $SO_3H$.

Another embodiment of the present invention concerns strontium salts of the compounds of formula (I) wherein B represents a substituted or unsubstituted linear $C_1$-$C_6$alkylene chain.

Another embodiment of the present invention concerns strontium salts of the compounds of formula (I) wherein B represents a substituted or unsubstituted linear $C_3$-$C_6$alkylene chain.

Another embodiment of the present invention concerns strontium salts of the sulphonic acids of formula (Ia), a particular case of the sulphonic acids of formula (I):

wherein:
A represents a group selected from $NH_2$ and $SO_3H$,
B represents an unsubstituted linear or branched $C_3$-$C_6$alkylene chain.

Another embodiment of the present invention concerns the following strontium salts:
strontium 1,3-propanedisulphonate;
strontium bis(3-amino-1-propanesulphonate);
strontium sulphonatoacetate;
strontium bis(2-amino-1-ethanesulphonate);
strontium 1,4-butanedisulphonate; and
strontium 1,2-benzenedisulphonate.

The invention relates also to a first process for the preparation of the strontium salts according to the invention by reaction of a sulphonic acid of formula (I):

wherein A and B are as defined hereinbefore,
with strontium hydroxide, followed by isolation of the strontium salt so obtained.

The invention relates also to a second process for the preparation of the strontium salts according to the invention by reaction of the sodium or potassium salt of a sulphonic acid of formula (I)

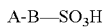
$$A\text{-}B\text{—}SO_3H \quad (I),$$

wherein A and B are as defined hereinbefore,
with strontium chloride, followed by isolation of the strontium salt so obtained.

The invention relates also to pharmaceutical compositions comprising as active ingredient a strontium salt according to the invention with one or more appropriate inert, non-toxic excipients, such as diluents, lubricants, binders, disintegrating agents, absorbers, colorants, sweetening agents etc.

By way of example and without implying any limitation there may be mentioned:

for the diluents: lactose, dextrose, sucrose, mannitol, sorbitol, cellulose, glycerol, for the lubricants: silica, talc, stearic acid and magnesium and calcium salts thereof, polyethylene glycol, for the binders: aluminium silicate, magnesium silicate, starch, gelatin, tragacanth, methyl cellulose, sodium carboxymethylcellulose, carboxymethyl starch and polyvinylpyrrolidone, for the disintegrating agents: agar, alginic acid and its sodium salt, effervescent mixtures.

Among the pharmaceutical compositions according to the invention there may be mentioned, more especially, those which are suitable for oral, parenteral (intravenous or subcutaneous) and nasal administration, tablets or dragées, sublingual tablets, gelatin capsules, lozenges, suppositories, creams, ointments, dermal gels, injectable preparations, drinkable suspensions.

The useful dosage varies according to the sex, age and weight of the patient, the administration route, the nature of the disorder and of associated treatments, if any, and ranges from 5 mg to 3 g per 24 hours, for example from 100 mg to 2 g per 24 hours.

The following Examples illustrate the invention.

EXAMPLE 1

Strontium 1,3-propanedisulphonate

A mixture of 222 g of 70% 1,3-propanedisulphonic acid in water (0.76 mol) and 200.4 g of strontium hydroxide octahydrate (0.75 mol) in 200 ml of water is heated at reflux for 3 hours. The reaction mixture is filtered hot and then cooled to 4° C. The precipitate formed is removed by filtration and 500 ml of 96% ethanol are added to the filtrate. The precipitate is filtered off, rinsed with 250 ml of a 70/30 ethanol/water mixture and dried to obtain 139 g of a white crystalline product of 1,3-propanedisulphonic acid strontium salt (yield 63%).

Melting point: >250° C.
Elemental Microanalysis:

|  | % C | % H | % S | % Sr |
|---|---|---|---|---|
| Calculated | 12.43 | 2.09 | 22.13 | 30.23 |
| Found | 12.56 | 3.44 | 22.76 | 26.88 |

EXAMPLE 2

Strontium bis(3-amino-1-propanesulphonate)

The expected product is obtained by reaction of 3-amino-1-propanesulphonic acid with strontium hydroxide octahydrate in accordance with the procedure of Example 1.

EXAMPLE 3

Strontium Sulphonatoacetate

The expected product is obtained by reaction of sulphoacetic acid with strontium hydroxide octahydrate in accordance with the procedure of Example 1.

Melting point: >270° C.
Elemental Microanalysis:

|  | % C | % H | % S |
|---|---|---|---|
| Calculated | 10.64 | 0.89 | 14.21 |
| Found | 9.77 | 1.20 | 14.18 |

EXAMPLE 4

Strontium bis(2-amino-1-ethanesulphonate)

The expected product is obtained by reaction of 2-amino-1-ethanesulphonic acid with strontium hydroxide octahydrate in accordance with the procedure of Example 1.

EXAMPLE 5

Strontium 1,4-butanedisulphonate 0.75 mol of strontium chloride hexahydrate and 0.75 mol of disodium 1,4-butane-disulphonate are dissolved in 600 ml of water. After stirring for 1 hour, 1 litre of 96% ethanol is added. The precipitate formed is filtered off, rinsed with 500 ml of a 70/30 ethanol/water mixture and dried to yield the expected product.

EXAMPLE 6

Strontium 1,2-benzenedisulphonate

The expected product is obtained by reaction of dipotassium 1,2-benzenedisulphonate with strontium chloride hexahydrate in accordance with the procedure of Example 6.

EXAMPLE 7

Strontium bis(2-hydroxyethanesulphonate)

The expected product is obtained by reaction of sodium 2-hydroxyethanesulphonate with strontium chloride hexahydrate in accordance with the procedure of Example 6.

EXAMPLE 8

Distrontium 2,2-bis(sulphonatomethyl)-1,3-propanedisulphonate

The expected product is obtained by reaction of 2,2-bis(sulphomethyl)-1,3-propanedisulphonic acid with strontium hydroxide octahydrate in accordance with the procedure of Example 1.

EXAMPLE 9

Strontium 1,5-pentanedisulphonate

The expected product is obtained by reaction of disodium 1,5-pentanedisulphonate with strontium chloride hexahydrate in accordance with the procedure of Example 6.

EXAMPLE 10

Strontium 1,6-hexanedisulphonate

The expected product is obtained by reaction of disodium 1,6-hexanedisulphonate with strontium chloride hexahydrate in accordance with the procedure of Example 6.

EXAMPLE 11

Strontium bis(4-amino-1-butanesulphonate)

The expected product is obtained by reaction of 4-amino-1-butanesulphonic acid with strontium hydroxide octahydrate in accordance with the procedure of Example 1.

EXAMPLE 12

Strontium bis(1-amino-2-benzenesulphonate)

The expected product is obtained by reaction of 1-amino-2-benzenesulphonic acid with strontium hydroxide octahydrate in accordance with the procedure of Example 1.

Pharmacological Study

EXAMPLE 13

In Vitro Study of the Inhibition of Bovine Cartilage Catabolism by the Compound of Example 1

Protocol

The study was carried out on fragments of bovine cartilage in culture medium (96-well plate), the degradation of which is stimulated by adding TNFα and oncostatin M (Schaller, S., Henriksen, K., Hoegh-Andersen, P., Sondergaard, B. C., Sumer, E. U., Tanko, L. B., Qvist, P., Karsdal, M. A. In vitro, ex vivo, and in vivo methodological approaches for studying therapeutic targets of osteoporosis and degenerative joint diseases: how biomarkers can assist? *Assay. Drug Dev. Technol.* 3, 553-580 (2005).

The duration of the cultivation period is 21 days (culture medium changed every 2 days). A group not treated with TNFα and oncostatin M constitutes the control group. Five lots of stimulated cartilage fragments were treated with the compound of Example 1, each at a different dose: 0.01; 0.1; 1; 3 and 10 mM. 5 replications were carried out for each dose.

On D19, the concentration of CTX II (fragment of type II collagen resulting from the degradation of that collagen by metalloproteases) in the culture medium is measured using an ELISA technique. That parameter is expressed in ng/ml/mg of cartilage.

On D21, the following are measured in the cartilage remaining at the end of cultivation:
  the quantity of proteins, using the kit marketed by Biorad. For the groups treated with the compound of Example 1, the results of this parameter are expressed as the percentage inhibition of the degradation of the proteins in the cartilage of the untreated control group;
  and the quantity of glycosaminoglycans (GAGs), using the calorimetric technique with methylene blue (DMB). That parameter, too, is expressed as a percentage inhibition of the degradation of the GAGs evaluated in the control group after culturing for 21 days.

Results

The results of treatment with the compound of Example 1 are:
  a significant ($p<0.001$) and dose-dependent inhibition of the salting out of CTX II in the culture medium ($IC_{50}=3.5$ mM);
  protection against degradation of the components of the cartilage starting from a dose of 1 mM:

| | Dose (mM) | | | | |
|---|---|---|---|---|---|
| Components | 0.01 | 0.1 | 1 | 3 | 10 |
| proteins | / | / | 22% | 41% | 55%* |
| GAGs | / | / | 4% | 8% | 26%** |

*$p < 0.05$;
**$p < 0.01$

The treatment is moreover well tolerated by the cells for the 21 days of cultivation (toxicity test employed: Alamar blue—negative whatever the dose).

Those results demonstrate that the compound of Example 1 provides significant protection against the degradation of the characteristic components of cartilage by way of inhibition of collagenolytic activity.

EXAMPLE 14

Pharmaceutical Composition

Preparation formula for a 1 g tablet containing a dose of 500 mg:
Compound of Example 1 . . . 500 mg
Povidone K30 . . . 24 mg
Cellulose Avicel PM102 . . . 417 mg
Carboxymethyl starch Primojel . . . 21 mg
Magnesium stearate . . . 6 mg
Talc . . . 32 mg

The invention claimed is:

1. A strontium salt of a sulfonic acid selected from those of formula (I):

$$A-B-SO_3H \quad (I)$$

wherein:
  A represents a group selected from $NH_2$ and $SO_3H$, and
  B represents an unsubstituted linear or branched $C_3$-$C_6$ alkylene chain.

2. The strontium salt according to claim 1, which is selected from:
  strontium 1,3-propanedisulphonate and
  strontium 1,4-butanedisulphonate.

3. A pharmaceutical composition comprising as active ingredient a strontium salt of a sulfonic acid selected from those of formula (I):

$$A\text{-}B\text{—}SO_3H \qquad (I),$$

wherein:

A represents a group selected from $NH_2$ and $SO_3H$, and

B represents an unsubstituted linear or branched $C_3$-$C_6$ alkylene chain, in combination with one or more pharmaceutically acceptable, inert non-toxic carriers.

4. A method of treating a living animal body, including a human, afflicted with osteoarthritis, comprising the step of administering to the living animal body, including a human, an amount of a strontium salt of a sulfonic acid selected from those of formula (I):

$$A\text{-}B\text{—}SO_3H \qquad (I),$$

wherein:

A represents a group selected from $NH_2$ and $SO_3H$, and

B represents an unsubstiuted unsubstituted linear or branched $C_3$-$C_6$ alkylene chain which is effective for treatment of osteoarthritis.

5. A method of treating a living animal body, including a human, afflicted with osteoporosis, comprising the step of administering to the living animal body, including a human, an amount of a strontium salt of a sulfonic acid selected from those of formula (I):

$$A\text{-}B\text{—}SO_3H \qquad (I),$$

wherein:

A represents a group selected from $NH_2$ and $SO_3H$, and

B represents an unsubstituted linear or branched $C_3$-$C_6$ alkylene chain, which is effective for treatment of osteoporosis.

* * * * *

UNITED STATES PATENT AND TRADEMARK OFFICE
CERTIFICATE OF CORRECTION

PATENT NO.         : 7,999,009 B2
APPLICATION NO.    : 11/784642
DATED              : August 16, 2011
INVENTOR(S)        : François Lefoulon et al.

Page 1 of 1

It is certified that error appears in the above-identified patent and that said Letters Patent is hereby corrected as shown below:

Column 8, Line 3:   "B represents an unsubstiuted unsubstituted linear or" should be --B represents an unsubstituted linear or--.

Signed and Sealed this
Eighteenth Day of October, 2011

David J. Kappos
*Director of the United States Patent and Trademark Office*